(12) United States Patent
Goudar

(10) Patent No.: US 6,218,545 B1
(45) Date of Patent: Apr. 17, 2001

(54) REGIOSELECTIVE FLUORINATION OF PHENYL-SUBSTITUTED TRIAZOLINONES

(75) Inventor: Jaidev Goudar, Plainsboro, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/385,120

(22) Filed: Aug. 27, 1999

Related U.S. Application Data

(60) Provisional application No. 60/098,060, filed on Aug. 27, 1998.

(51) Int. Cl.$^7$ .................................................. C07D 249/12
(52) U.S. Cl. ..................... 548/263.2; 548/263.4; 548/263.8
(58) Field of Search .............................. 548/263.2, 263.4, 548/263.8

(56) References Cited

U.S. PATENT DOCUMENTS

| 4,980,480 | 12/1990 | Theodoridis et al. | 548/263.2 |
|---|---|---|---|
| 5,438,149 | 8/1995 | Halfon et al. | 548/263.2 |
| 5,756,755 | 5/1998 | Goudar | 548/263.2 |

OTHER PUBLICATIONS

J. Chem. So., Chem. Commun., 1992, p. 595–596.
Chem. Rev., 1996, 96, 1737–1755.
J. Org. Chem., 1993, 58, 2791–2796.

Primary Examiner—Patricia L. Morris
(74) Attorney, Agent, or Firm—FMC Corporation

(57) ABSTRACT

A process for the preparation of a compound of the Formula I

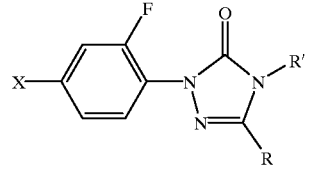

Formula I wherein
the process comprising the step of treating a compound of the Formula II

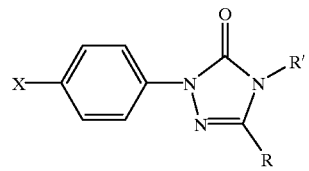

Formula II with a fluorinating agent at a temperature of about 60° to about 120° C. in the presence of an organic solvent to form a compound of the Formula I; wherein:

X, R or R' can optionally be independently protected with a protecting group which is substantially stable to the fluorinating agent; and where X, R, and R' are described herein.

13 Claims, No Drawings

REGIOSELECTIVE FLUORINATION OF PHENYL-SUBSTITUTED TRIAZOLINONES

This application claims benefit of U.S. Provisional Application No. 60/098,060, filed Aug. 27, 1998.

The present invention relates generally to processes for preparing 1-(2-fluorophenyl)-substituted triazolinones. In particular, it pertains to the fluorination of the phenyl ring of 4,5-dihydro-1-(4-substituted phenyl)-3,4-disubtituted-1,2,4-triazol-5(1H)-ones.

The 4,5-dihydro-1-(2-fluoro substituted phenyl)-3,4-disubtituted-1,2,4-triazol-5(1H)-ones, for example 4,5-dihydro-1-(4-chloro-2-fluorophenyl)-3-methyl-4-difluoromethyl-1,2,4-triazol-5(1H)-one, are critical intermediates in the manufacture of fine chemicals, such as pesticides. For example, 4,5-dihydro-1-(4-chloro-2-fluorophenyl)-3-methyl-4-difluoromethyl-1,2,4-triazol-5 (1H)-one is a known intermediate in the manufacture of the herbicide ethyl α-2dichloro-5-[4-(difluoromethyl)-4,5-dihydro-3-methyl-5-oxo-1H-1,2,4-triazol-1yl]-4-fluorobenzenepropanoate.

Fluorination of complex aromatic systems is difficult because of fluorine's high reactivity. As a result, there are only a few practical commercial methods by which fluorine can be introduced regioselectively into complex aromatic systems.

One method of fluorination includes the Balz-Schiemann reaction in which an aromatic ring is fluorinated by the thermal decomposition of diazonium fluoroborates. This method has failed to provide the desired product in appreciable yield.

Another method for the preparation of fluorinated complex aromatic systems, in particular phenyl-substituted triazolinones, includes the use of 2-fluoroaniline or 2-fluorophenylhydrazine as starting materials for the preparation of a corresponding 1-(2-fluorophenyl)-substituted triazolinones thereby avoiding the difficult task of fluorinating a deactivated aromatic ring. These procedures provide low synthetic yields.

Electrophilic NF fluorinating agents have been used to directly fluorinate monosubstituted and disubstituted aromatics to provide mixtures of the ortho- and para-fluorophenyl substituted compounds. (*J. Chem. Soc., Chem. Commun.*, 1992, pg. 595–596). Substantially isomerically pure para-fluoro-trisubstituted aromatic rings have been prepared with this procedure when at least one of the substituents of the disubstituted aromatic starting material is electron donating. This procedure has not been applied to the preparation of 1-(2-fluoro-4-substituted-phenyl)-3,4-disubstituted triazolinones.

There remains a need for a simple and generally high yielding method for the preparation of the key synthetic intermediates 1-(2-fluoro-4-substituted-phenyl)-3,4-disubstituted triazolinones in substantially isomerically pure or isomerically enriched form using 1-(4-substituted-phenyl)-3,4-disubstituted triazolinones as starting materials.

SUMMARY OF THE INVENTION

The present invention provides a method by which fluorine can be regioselectively introduced into complex aromatic systems. The present invention provides a method for the preparation of 4,5-dihydro-1-(2-fluoro-4-substituted phenyl)-3,4-disubtituted-1,2,4-triazol-5(1H)-one of the Formula I below by the direct fluorination of a corresponding 4,5-dihydro-1-(4-substituted phenyl)-3,4-disubstituted-1,2,4-triazol-5(1H)-one of the Formula II with a fluorinating agent in the presence of an organic solvent.

The present invention provides a high degree of regioselectivity in the fluorination of complex aromatic systems by preferentially fluorinating the pendant phenyl group of the compound of the Formula II at the ortho-position rather than the meta- or para-positions. Treatment of a compound of the Formula II with a fluorinating agent provides a corresponding compound of the Formula I in moderate yields.

It has been unexpectedly found that the fluorination process of the present invention can provide compounds of the Formula I in high regioselective and chemical yield containing less than about 10% by weight, preferably less than about 5% by weight, more preferably less than about 2% by weight, and most preferably no detectable amount, of undesired regioisomers.

In one embodiment, the invention provides a process for the preparation of a compound of the Formula I

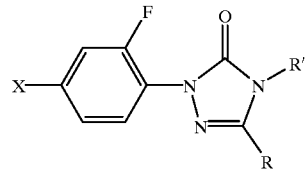

Formula I wherein:
X is hydrogen, halogen, $C_1$–$C_6$-alkyl, $C_1$–$C_6$-haloalkyl, or nitro; and
R and R' are independently hydrogen, halo, $C_1$–$C_6$-alkyl, $C_2$–$C_6$-alkenyl, $C_3$–$C_5$-alkynyl, $C_1$–$C_6$-haloalkyl, $C_2$–$C_6$-haloalkenyl, $C_2$–$C_7$-acyl, $C_2$–$C_6$-alkoxyalkyl, $C_2$–$C_6$-cyanoalkyl, $C_1$–$C_3$-alkylsulfinyl, $C_1$–$C_3$-alkylsulfonyl, or $C_1$–$C_3$-alkylthio-$C_1$–$C_3$-alkyl;
the process comprising the step of treating a compound of the Formula II

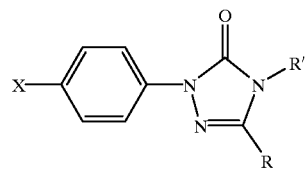

Formula II with a fluorinating agent at a temperature of about 60° to about 120° C. in the presence of an organic solvent to form a compound of the Formula I; wherein:
X and R are as defined above;
R' is independently an alkali metal cation, hydrogen, halo, $C_1$–$C_6$-alkyl, $C_2$–$C_6$-alkenyl, $C_3$–$C_5$-alkynyl, $C_1$–$C_6$-haloalkyl, $C_2$–$C_6$-haloalkenyl, $C_2$–$C_7$-acyl, $C_2$–$C_6$-alkoxyalkyl, $C_2$–$C_6$-cyanoalkyl, $C_1$–$C_3$-alkylsulfinyl, $C_1$–$C_3$-alkylsulfonyl, or $C_1$–$C_3$-alkylthio-$C_1$–$C_3$-alkyl; and
X, R or R' can optionally be independently protected with a protecting group which is substantially stable to the fluorinating agent.

In another embodiment, R and R' are independently hydrogen, halo, $C_1$–$C_6$-alkyl, $C_2$–$C_6$-alkyl, $C_1$–$C_6$-haloalkyl, $C_2$–$C_6$-haloalkyl or $C_2$–$C_7$-acyl.

In yet another embodiment, X is H or halogen; R is $C_1$–$C_6$-alkyl; and R' is $C_1$–$C_6$-haloalkyl. In still yet another embodiment, X is chloro; R is methyl; and R' is difluoromethyl.

DETAILED DESCRIPTION OF THE INVENTION

The yields of the present process depend, among other things, upon the temperature at which the treatment is conducted, the mode, rate or order of addition into a reaction vessel of the fluorinating agent and the compound of the Formula II, the molar ratio of the fluorinating agent to the compound of the Formula II, or the solvent employed or a catalyst employed.

The process of the present invention can be run at temperatures ranging from about 60° C. to a temperature which is at or below the boiling point of the organic solvent(s) used. The optimal temperature for running the fluorination reaction will depend, among other things, upon the organic solvent or combination of organic solvents used to run the reaction. The optimal temperature will generally range from about 60° to about 120° C., preferably from about 80° to about 115° C., more preferably from about 80° to about 85° C.

The modifier "about" is used herein to indicate that certain preferred operating ranges, such as material amounts and temperature, and ranges thereof, are not fixedly determined. The meaning will often be apparent to one of ordinary skill. For example, a recitation of a temperature range of about 60° C. to about 120° C. in reference to, for example, the aforementioned fluorination reaction would be interpreted to include other like temperatures which can be expected to favor a useful rate of reaction, such as, for example, 54° C. or 132° C. Where guidance from the experience of those of ordinary skill is lacking, guidance from the context is lacking, and where a more specific rule is not recited below, the "about" range shall be not more than 10% of the absolute value of an end point or 15% of the range recited, whichever is less.

Fluorinating agents that may be used in accordance with the present invention are electrophilic NF reagents and xenon difluoride. NF reagents are electrophilic fluorinating agents that contain a fluorine atom bound to a nitrogen atom which is part of an organic compound. NF reagents serve as $F^+$ transfer agents. The NF fluorinating reagents used in the present invention can include those described by Lal et al. (*Chem. Rev.*, 1996, 96, 1737–1755), Lal (*J. Org. Chem*, 1993, 58, 2791–2796), and Banks et al. (*J. Chem. Soc., Chem. Commun.* 1992, 595–596), the relevant disclosures of which are hereby incorporated by reference. Examples of electrophilic NF reagents include but are not limited to fluorine triethylenediamine (F-TEDA), N-fluoro-o-benzenesulfonimide, and N-fluoro-2-pyridone.

The electrophilic NF reagent can include any of the following:

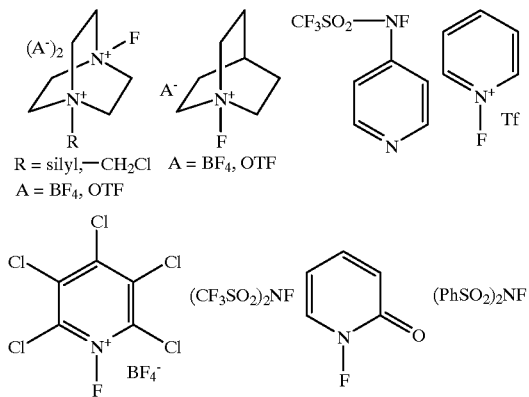

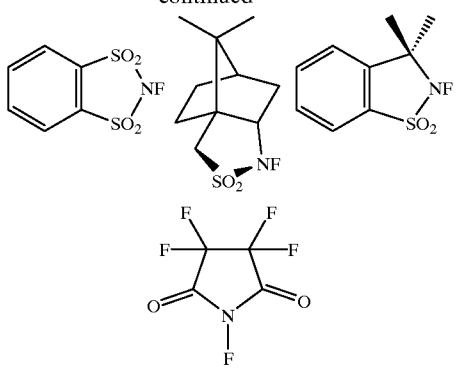

In a particular embodiment, the fluorinating agent is fluorine triethylenediamine.

The fluorinating agent can be added to the fluorination reaction mixture in a single portion, in at least two portions, or continuously as either a solid or solution containing the fluorinating agent. For example, the fluorinating agent can be added as a powdered solid in two or more portions, or it can be added continuously to the fluorination reaction, as a solution or suspension comprising an organic solvent and the fluorinating agent, by way of a syringe, peristaltic or metering pump. The amount, in terms of molar equivalents, of fluorinating agent in each aliquot or portion can be varied as desired.

The process of the invention can be run at ambient to elevated pressure or generally from about atmospheric pressure or 1 atmosphere to about 10 atmospheres. The fluorination reaction can be accelerated by increasing the pressure under which the reaction is run.

The process of the invention is run for a period of time sufficient to form the compound of the Formula I. The fluorination reaction time preferably ranges from about 4 to about 72 hours for completion, more preferably from about 6 to about 48 hours, and can vary according to the reaction temperature, the solvent employed, the presence or absence of a catalyst, the structure of the compound of the Formula I, the fluorinating agent employed and other factors. For example, the fluorination reaction is generally faster when R' is hydrogen than when R' is difluoromethyl.

The concentration of a compound of the Formula II in the reaction solvent can range from about 5% to about 25%, preferably from about 10% to about 25%, more preferably from about 15% to about 20% by weight, based upon the final weight of the reaction mixture. Generally, about 5 to about 50, preferably about 10 to about 30, volumes mL or L of solvent per g or Kg, respectively, of the compound of the Formula II are used.

The compound of the Formula I can be isolated from the reaction mixture and purified according to the methods disclosed in Example 1 or according to other methods known to those of skill in the art. For example, the solvent can be evaporated or otherwise removed from the reaction mixture to form a residue, and the compound of the Formula I can be isolated from the resulting residue by vacuum distillation or sublimation.

A wide range of organic solvents can be employed in the presently claimed process. The organic solvent will generally be able to dissolve at least a portion of either one or both of the compound of the Formula I and the fluorinating agent. The organic solvents that may be useful in the present invention include, but are not limited to, acetonitrile, xylene, nitrobenzene, ethyl acetate, dichloromethane, N,N-dimethylformamide (DMF), tetrahydrofuran (THF), aqueous solutions of the above solvents which are water-miscible, and combinations thereof. In one embodiment, the organic solvent is acetonitrile.

Suitable halogenated solvents include: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, and o-dichlorobenzene.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl ethyl ether, and t-butyl methyl ether.

Suitable protic solvents may include, by way of example and without limitation, water, ethylene glycol, diethylene glycol, diethylene glycol monomethyl ether, diethylene glycol monoethyl ether, anisole, and glycerol.

Suitable aprotic solvents may include, by way of example and without limitation, dimethylformamide (DMF), dimethylacetamide (DMAC), 1,3-dimethyl-3,4,5,6-tetrahydro-2(1H)-pyrimidinone (DMPU), formamide, ethyl formate, 1,3-dimethyl-2-imidazolidinone (DMI), N-methylpyrrolidinone (NMP), N-methylacetamide, N-methylformamide, acetonitrile, dimethyl sulfoxide, propionitrile, methyl acetate, ethyl methyl ketone, ethyl acetate, sulfolane, N,N-dimethylpropionamide, tetramethylurea, nitrobenzene, and hexamethylphosphoramide.

Suitable acidic solvents include, by way of example and without limitation, trifluoroacetic acid and acetic acid.

Suitable hydrocarbon solvents include, by way of example and without limitation, cyclohexane, pentane, hexane, cycloheptane, methylcyclohexane, heptane, octane, indane, and nonane.

The present process can be run in the solution phase or in a biphasic, i.e., solid/liquid or liquid/liquid, reaction system. When a biphasic reaction system is employed, a phase transfer catalyst can be used to aid in the dissolution of the either one or both the fluorinating agent and the compound of the Formula II in the liquid phase. Such phase transfer catalysts include those disclosed in Starks et al., "Phase-Transfer Catalysis: Fundamentals, Applications, and Industrial Perspectives" (Chapman & Hall, NY; 1994), the disclosure of which is hereby incorporated by reference.

Generally, the fluorination of a compound of the Formula II in a suitable solvent, such as those recited hereinabove, and most preferably acetonitrile, with at least two aliquots each of about 0.8 to about 1.6, preferably about one, molar equivalent of a fluorinating agent provides yields of about 50% to about 70% of theoretical yield of a compound of the Formula I within from about 4 to about 72 hours, preferably about 6 to about 48 hours from the onset of reaction.

When necessary, the groups X, R and/or R' can be independently protected with a suitable protecting group which is substantially stable to the fluorinating agent and/or the reaction conditions of the fluorination process of the present invention. As used herein, the term "protecting group" refers to any of a number of chemical protecting groups known to those of ordinary skill in the art, which groups are used to protect radicals or substituents, such as X, R and/or R', from degradation by a fluorinating agent and/or reaction conditions of fluorination. Such groups include, but are not limited to those disclosed in Greene and Wuts, "Protective Groups in Organic Synthesis" (John Wiley & Sons NY; 1991), the relevant disclosure of which is hereby incorporated by reference.

As used herein and unless otherwise indicated, the term "alkyl", when used alone or as part of a larger moiety, includes one to six, preferably one to four, carbon atoms. As used herein and unless otherwise indicated, the term "alkenyl", when used alone or as part of a larger moiety, includes two to six, preferably two to four, carbon atoms. The terms alkyl and alkenyl should be understood to include the straight chain, branched and cyclic forms of those groups.

As used herein and unless otherwise indicated, the terms "haloalklyl" and "haloalkenyl" refer to alkyl or alkenyl groups, respectively, as defined above which are substituted by one or more halogens. Such haloalkyl groups include, but are not limited to, fluoromethyl, difluoromethyl, trifluoromethyl, difluorochloromethyl, fluoropropyl, and difluoroethyl. Such haloalkenyl groups include, but are not limited to, fluoroethylenyl, bromopropylenyl, bromoethylenyl, dichloroethylenyl, dibromoethylenyl, bromobutanyl, chlorobutenyl, and dibromobutenyl.

As used herein and unless otherwise indicated, the term acyl refers to a substituent having a carbonyl group attached to a $C_1$–$C_6$ alkyl or a $C_2$–$C_6$ alkenyl, wherein the carbonyl group is attached to the triazolinone ring.

As used herein and unless otherwise indicated, the terms "halogen" or "halo" refers to fluorine, bromine, chlorine, or iodine.

It will be appreciated that certain compounds of the present invention can contain an asymmetrically substituted carbon atom, and may be isolated in optically active or racemic forms. It is well known in the art how to prepare optically active forms, such as by resolution of racemic forms or by synthesis, from optically active starting materials. Many geometric isomers of olefins and the like can also be present in the compounds described herein, and all such stable isomers are contemplated in the present invention. Also, it is realized that cis and trans geometric isomers of the compounds of the present invention are described and may be isolated as a mixture of isomers or as separated isomeric forms. All chiral, diastereomeric, and racemic forms of the compounds of the Formulae I and II are included in the present invention.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that any one or more hydrogens on the designated atom is replaced with a selection from the indicated group, provided that the designated atom's normal valency is not exceeded, and that the substitution results in a stable compound.

The compound of the Formula II was prepared according to Example 2 below and according to the procedures described in U.S. Pat. Nos. 4,980,480 and 5,468,868, the disclosures of which are hereby incorporated by reference. Unless otherwise noted, all other materials used herein are commercially available from sources such as Aldrich Chemical Co., Inc., Aceto Corporation, Acros Organics, Air Products, Apollo Scientific, Ltd., Albright & Wilson Americas, Bachem, AlliedSignal Corporation, BASF Aktiengesellschaft, Borregaard Fine Chemicals, Bridgewater Chemical, BNFL Fluorochemicals Ltd., Eastman Chemical Company, Elan Incorporated, Fluorochem Ltd., Fluka Chemie AG, Fisher Scientific, INDOFINE Chemical Company, Inc., JRD Fluorochemicals Ltd., Kanto Chemicals Co., Inc., Lancaster Synthesis Ltd., Research Organics Inc., Strem Chemicals, Inc., Wychem Ltd., or VWR Scientific.

The foregoing will be better understood with reference to the following examples which detail certain procedures for the manufacture of triazolinones according to the present invention. All references made to these examples are for the purposes of illustration. They are not to be considered limiting as to the scope and nature of the present invention because further modifications of the disclosed invention will be apparent to those skilled in the art. All such modifications are deemed to be within the scope of the present invention.

EXAMPLE 1

Preparation of the Compound of the Formula I: 4,5-Dihydro-1-(4-chloro-2-fluorophenyl)-3-methyl-4-difluoromethyl-1,2,4-triazol-5(1H)-one Under a nitrogen atmosphere, a stirred solution of 5.0 grams (0.0192 mole—1.0 equiv.) of 4,5-Dihydro-1-(4-chlorophenyl)-3-methyl-4-difluoromethyl-1,2,4-triazol-5(1H)-one and 6.8 grams (0.0192 mole—1.0 equiv.) of F-TEDA in 50 mL of acetonitrile (% Wt/Vol triazolinone to solvent—10%) was stirred at 82° C. for 24 hours. After this time, an additional 6.8 grams (0.0192 mole—1.0 equiv.) of F-TEDA was added. Upon completion of addition, the reaction mixture was stirred at 82° C. for an additional 24 hours. The reaction mixture was analyzed by gas chromatography (GC), which indicated the reaction was 78% complete. The reaction mixture was cooled to ambient temperature, and the acetonitrile was removed under reduced pressure. The resulting residue was taken up in 30 mL of water and then 40 mL of an aqueous 10% hydrochloric acid solution was added. The resulting solution was extracted with three 30 mL portions of ethyl acetate. The organic layer was separated from the aqueous layer, dried with magnesium sulfate, and filtered. The filtrate was concentrated under reduced pressure, yielding 2.9 grams (48% yield) of title compound. The $H^1$ NMR spectrum of the product was consistent with that of a reference sample.

EXAMPLE 2

Preparation of the compound of the Formula II: 4,5-dihydro-3-methyl-1-(4-chlorophenyl)-1,2,4-triazol-5(1H)-one and 4,5-dihydro-3-methyl-1-phenyl-1,2,4-triazol-5(1H)-one The following procedure is described in U.S. Pat. No. 4,980,480.

Chlorine gas was bubbled into a solution of 17.7 g (0.1 mol) of 3-methyl-1-phenyl-1,2,4-triazolidin-5-one in about 10 times its weight of glacial acetic acid at room temperature for 5 minutes. The temperature rose to 35° C., and the brown solution became lighter in color. NMR analysis showed that the product was 4,5-dihydro-3-methyl-1-phenyl-1,2,4-triazol-5(1H)one. Next 1.0 g of iron powder was slowly added to the mixture which was then heated to 95° C. Chlorine gas was bubbled into it for 10 minutes, after which it was maintained at the elevated temperature for one hour while stirring. The mixture was then dumped into ice, extracted with ethyl acetate, dried over magnesium sulfate and passed through a column of silica gel (which was then eluted with 200 ml of ethyl acetate to give a solution from which the solvent was then evaporated under reduced pressure), giving 12.0 g of a solid (m.p. 174°–176° C.), 4,5-dihydro-3-methyl-1-(4-chlorophenyl)-1,2,4-triazol-5(1H)-one. The $H^1$ NMR spectrum of the product was consistent with that of a reference sample.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

I claim:

1. A process for the preparation of a compound of the Formula I

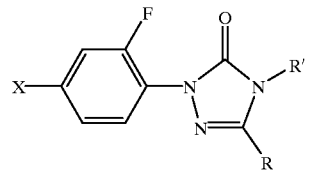

Formula I wherein:

X is hydrogen, halogen, $C_1$–$C_6$-alkyl, $C_1$–$C_6$-haloalkyl, or nitro; and

R and R' are independently hydrogen, halo, $C_1$–$C_6$-alkyl, $C_2$–$C_6$-alkenyl, $C_3$–$C_5$-alkynyl, $C_1$–$C_6$-haloalkyl, $C_2$–$C_6$-haloalkenyl, $C_2$–$C_7$-acyl, $C_2$–$C_6$-alkoxyalkyl, $C_2$–$C_6$-cyanoalkyl, $C_1$–$C_3$-alkylsulfinyl, $C_1$–$C_3$-alkylsulfonyl, or $C_1$–$C_3$-alkylthio-$C_1$–$C_3$-alkyl;

the process comprising the step of treating a compound of the Formula II

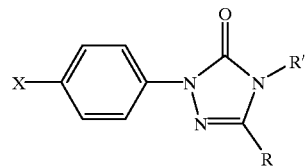

Formula II with a fluorinating agent at a temperature of from about 60° to about 120° C. in the presence of an organic solvent to form a compound of the Formula I; wherein:

X and R are as defined above;

R' is independently an alkali metal cation, hydrogen, halo, $C_1$–$C_6$-alkyl, $C_2$–$C_6$-alkenyl, $C_3$–$C_5$-alkynyl, $C_1$–$C_6$-haloalkyl, $C_2$–$C_6$-haloalkenyl, $C_2$–$C_7$-acyl, $C_2$–$C_6$-alkoxyalkyl, $C_2$–$C_6$-cyanoalkyl, $C_1$–$C_3$-alkylsulfinyl, $C_1$–$C_3$-alkylsulfonyl, or $C_1$–$C_3$-alkylthio-$C_1$–$C_3$-alkyl; and the fluorinating agent is selected from the group consisting of:

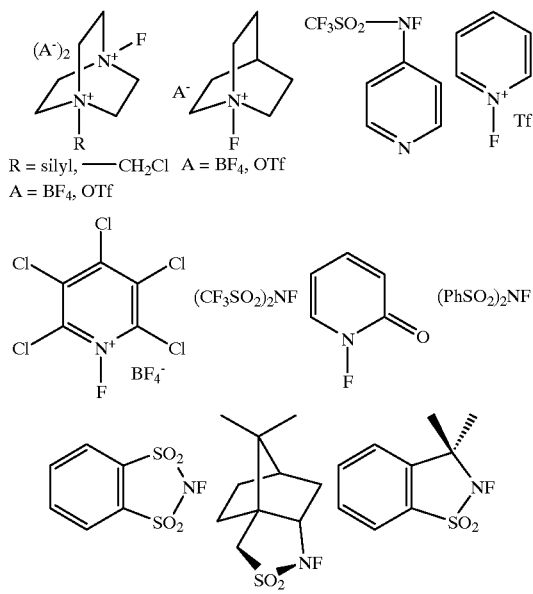

-continued

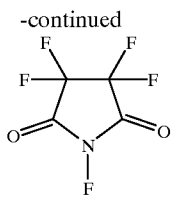

xenon difluoride, fluorine triethylenediamine, N-fluoro-0-benzensulfonimide, and N-fluoro-2-pyridone.

2. The process of claim 1, wherein X is halogen; R is $C_1$–$C_6$-alkyl; and R' is $C_1$–$C_6$-haloalkyl.

3. The process of claim 1, wherein X is chloro; R is methyl; and R' is difluoromethyl.

4. The process of claim 1, wherein the electrophilic NF reagent is fluoro triethylenediamine.

5. The process of claim 1, wherein R and R' are independently hydrogen, halo, $C_1$–$C_6$-alkyl, $C_2$–$C_6$-alkyl, $C_1$–$C_6$-haloalkyl, $C_2$–$C_6$-haloalkyl or $C_2$–$C_7$-acyl.

6. The process of claim 1, wherein the organic solvent is acetonitrile, xylene, nitrobenzene, ethyl acetate, dichloromethane, N,N-dimethylformamide, tetrahydrofuran, or an aqueous mixture containing one or more of said organic solvents.

7. The process of claim 1, wherein the organic solvent is acetonitrile.

8. The process of claim 1, wherein the compound of the Formula II is treated with the fluorinating agent at a temperature of about 60° to about 100° C. for a period of from about 4 to about 72 hours.

9. The process of claim 1, wherein the compound of the Formula II in acetonitrile is treated with the fluorinating agent at a temperature of from about 80° to about 85° C. for a period of from about 6 to about 48 hours.

10. The process of claim 1, wherein the compound of the Formula II is treated with at least two separate aliquots of from about 0.8 to about 1.6 molar equivalents each of fluorinating agent per mole of compound of the Formula II.

11. The process of claim 1, wherein X is chloro, R is methyl, R' is difluoromethyl, and the organic solvent is acetonitrile.

12. The process of claim 1, wherein the alkali metal cation is $Li^+$, $Na^+$ or $K^+$.

13. A process for the preparation of a compound of the Formula I

Formula I

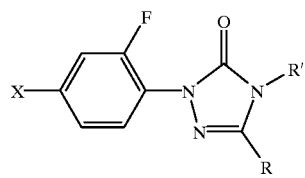

wherein:
X is hydrogen, halogen, $C_1$–$C_6$-alkyl, $C_1$–$C_6$-haloalkyl, or nitro; and
R and R' are independently hydrogen, halo, $C_1$–$C_6$-alkyl, $C_2$–$C_6$-alkenyl, $C_3$–$C_5$-alkynyl, $C_1$–$C_6$-haloalkyl, $C_2$–$C_6$-haloalkenyl, $C_2$–$C_7$-acyl, $C_2$–$C_6$-alkoxyalkyl, $C_2$–$C_6$-cyanoalkyl, $C_1$–$C_3$-alkylsulfinyl, $C_1$–$C_3$-alkylsulfonyl, or $C_1$–$C_3$-alkylthio-$C_1$–$C_3$-alkyl;

the process comprising the step of treating a compound of the Formula II

Formula II

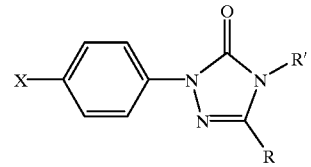

with an electrophilic NF reagent or xenon difluoride at a temperature of from about 60° to about 120° C. in the presence of an organic solvent to form a compound of the Formula I;

wherein:

X and R are as defined above;

R' is independently an alkali metal cation, hydrogen, halo, $C_1$–$C_6$-alkyl, $C_2$–$C_6$-alkenyl, $C_3$–$C_5$-alkynyl, $C_1$–$C_6$-haloalkyl, $C_2$–$C_6$-haloalkenyl, $C_2$–$C_7$-acyl, $C_2$–$C_6$-alkoxyalkyl, $C_2$–$C_6$-cyanoalkyl, $C_1$–$C_3$-alkylsulfinyl, $C_1$–$C_3$-alkylsulfonyl, or $C_1$–$C_3$-alkylthio-$C_1$–$C_3$-alkyl; and the electrophilic NF reagent is selected from the group consisting of:

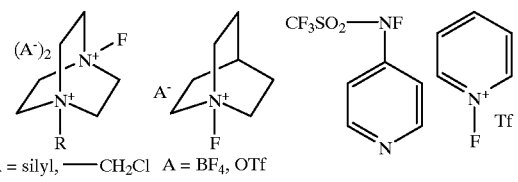

R = silyl, —CH$_2$Cl  A = BF$_4$, OTf
A = BF$_4$, OTf

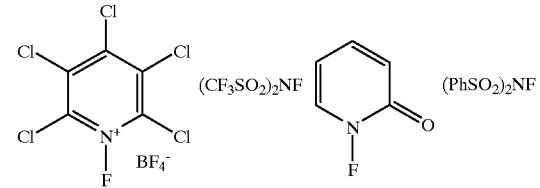

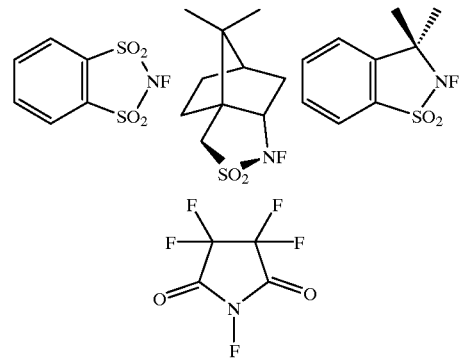

fluorine triethylenediamine, N-fluoro-0-benzensulfonimide, and N-fluoro-2-pyridone.

* * * * *